US00PP31491P3

(12) United States Plant Patent
van Langen

(10) Patent No.: US PP31,491 P3
(45) Date of Patent: Feb. 25, 2020

(54) ***ECHEVERIA* PLANT NAMED 'TSAECH1820'**

(50) Latin Name: ***Echeveria* hybrid**
Varietal Denomination: TSAECH1820

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/501,054

(22) Filed: Feb. 14, 2019

(65) Prior Publication Data

US 2019/0320572 P1 Oct. 17, 2019

(30) Foreign Application Priority Data

Apr. 13, 2018 (QZ) ..... PBR 2018/1026

(51) Int. Cl.
*A01H 5/12* (2018.01)
*A01H 6/00* (2018.01)
*A01H 6/32* (2018.01)

(52) U.S. Cl.
USPC ..... Plt./373
CPC ..... *A01H 6/00* (2018.05); *A01H 5/12* (2013.01); *A01H 6/32* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Echeveria* plant named 'TSAECH1820' which is characterized by improved plant vigor, an abundance of succulent foliage tightly held in a compact stemless rosette, heavily glaucous foliage at and near the center of the rosette which generally appears to be a mixture of blue-gray and greyed-green, foliage towards the outer whorls of the rosette which becomes decreasingly glaucous and therefore progressively darker, closer to greyed-green, foliage which is conspicuously margined and tipped pink, and the stability of these characteristics from generation to generation.

4 Drawing Sheets

CROSS REFERENCE TO RELATED APPLICATIONS

This application claims priority to the Community Plant Variety Rights application number 2018/1026, filed Apr. 13, 2018, which is herein incorporated by reference.

Latin name of the genus and species: The Latin name of the genus and species of the novel variety disclosed herein is *Echeveria* hybrid.

Variety denomination: The inventive variety of *Echeveria* disclosed herein has been given the variety denomination 'TSAECH1820'.

BACKGROUND OF THE INVENTION

Parentage: 'TSAECH1820' is a seedling selection resulting from the controlled pollination of an unnamed and unpatented *Echeveria pulidonis* plant, the seed parent, with an unnamed and unpatented *Echeveria laui* plant, the pollen parent. The crossing was made by the inventor in the spring of 2014 at a commercial greenhouse in Heerhugowaard, the Netherlands. In the summer of 2015, one seedling resulting from the cross of 2014 was observed to exhibit unique growth and foliage characteristics and was isolated for further evaluation in order to confirm the distinctness and stability of the characteristics first observed. Upon confirmation of distinctness and stability, 'TSAECH1820' was selected for commercialization.

Asexual Reproduction: Asexual reproduction of the new cultivar 'TSAECH1820', by way of rooting leaf cuttings, was first initiated in the spring of 2016 at the inventor's commercial greenhouse in Heerhugowaard, the Netherlands. Through four subsequent generations, the unique features of this cultivar have proven to be stable and true to type.

SUMMARY OF THE INVENTION

The cultivar 'TSAECH1820' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1820'. These characteristics in combination distinguish 'TSAECH1820' as a new and distinct *Echeveria* cultivar:

1. 'TSAECH1820' exhibits improved plant vigor, with lower mortality rates under adverse climatic conditions; and
2. 'TSAECH1820' exhibits an abundance of succulent foliage tightly held in a compact stemless rosette; and
3. 'TSAECH1820' exhibits heavily glaucous foliage at and near the center of the rosette, the color of which has a general appearance of a mixture between blue-grey and greyed-green; and
4. 'TSAECH1820' exhibits foliage towards the outer whorls of the rosette which becomes decreasingly glaucous and therefore progressively darker, closer to greyed-green; and 5. 'TSAECH1820' exhibits foliage which is conspicuously margined and tipped pink.

BOTANICAL DESCRIPTION OF THE PLANT

Figure 1:
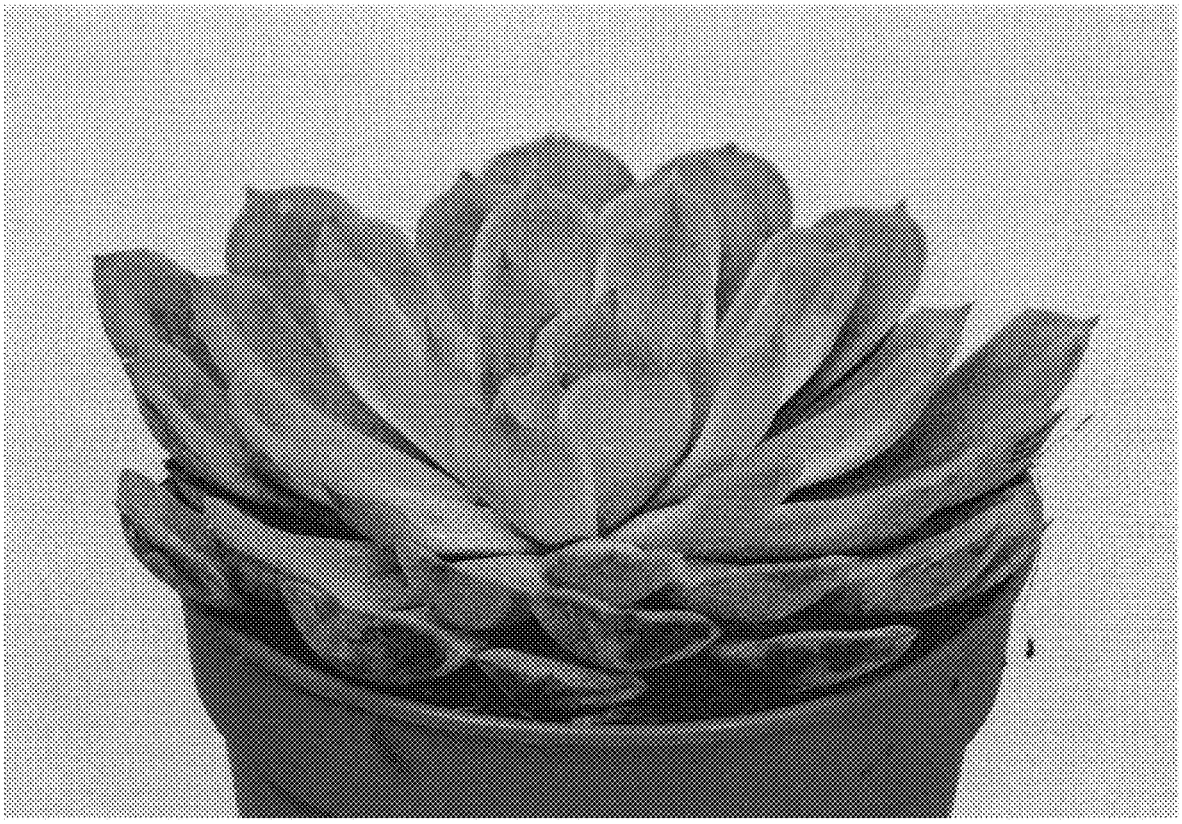
FIG. 1 illustrates, as nearly true as it is reasonably possible to make the same in color photographs of this type, an exemplary plant of 'TSAECH1820' grown in a commercial greenhouse in Heerhugowaard, the Netherlands. This plant is approximately 12 months old, shown planted in a 12 cm container.
Figure 2:
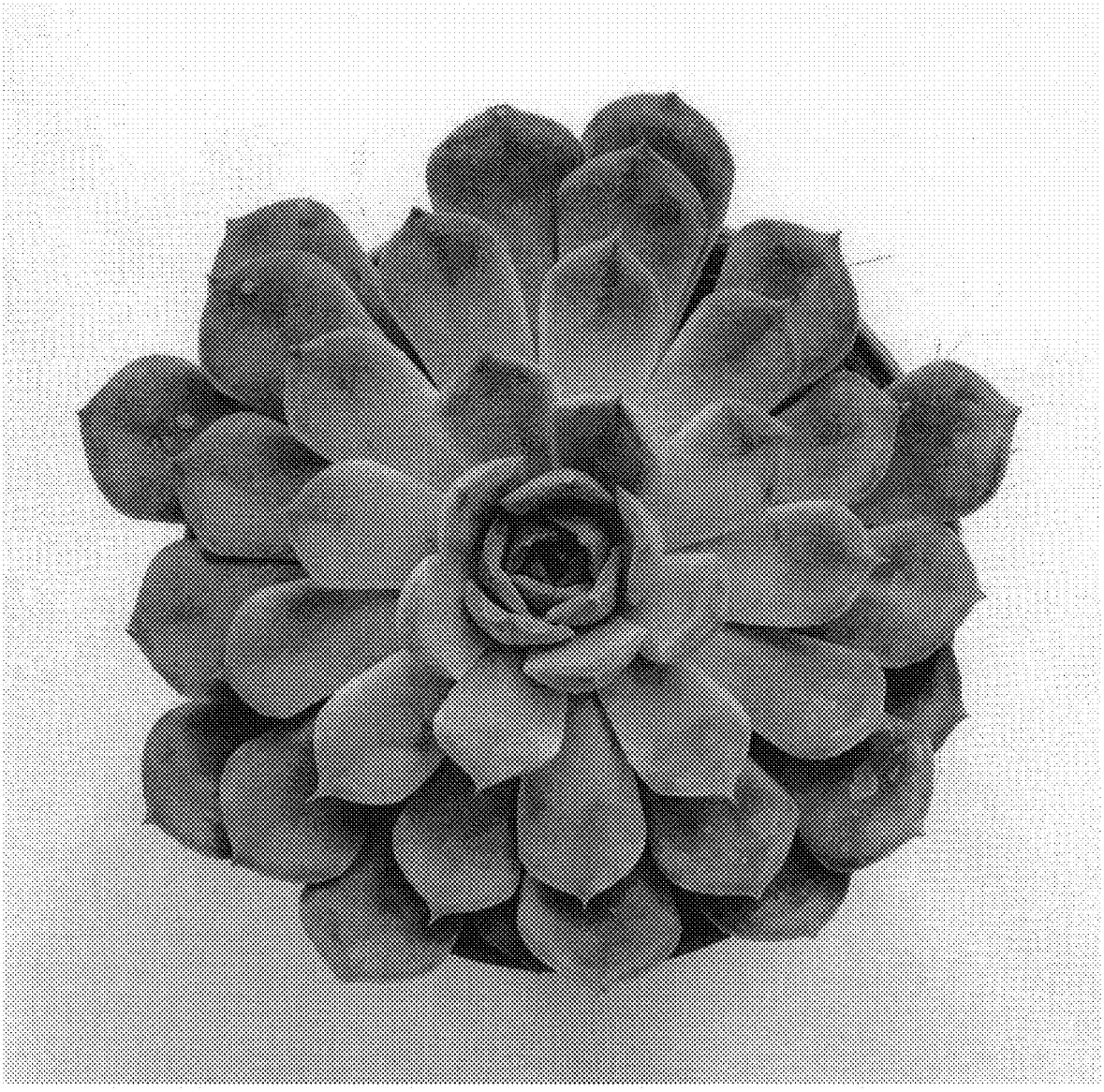
FIG. 2 illustrates, as nearly true as it is reasonably possible to make the same in color photographs of this type, the typical foliage arrangement of 'TSAECH1820.
Figure 3:
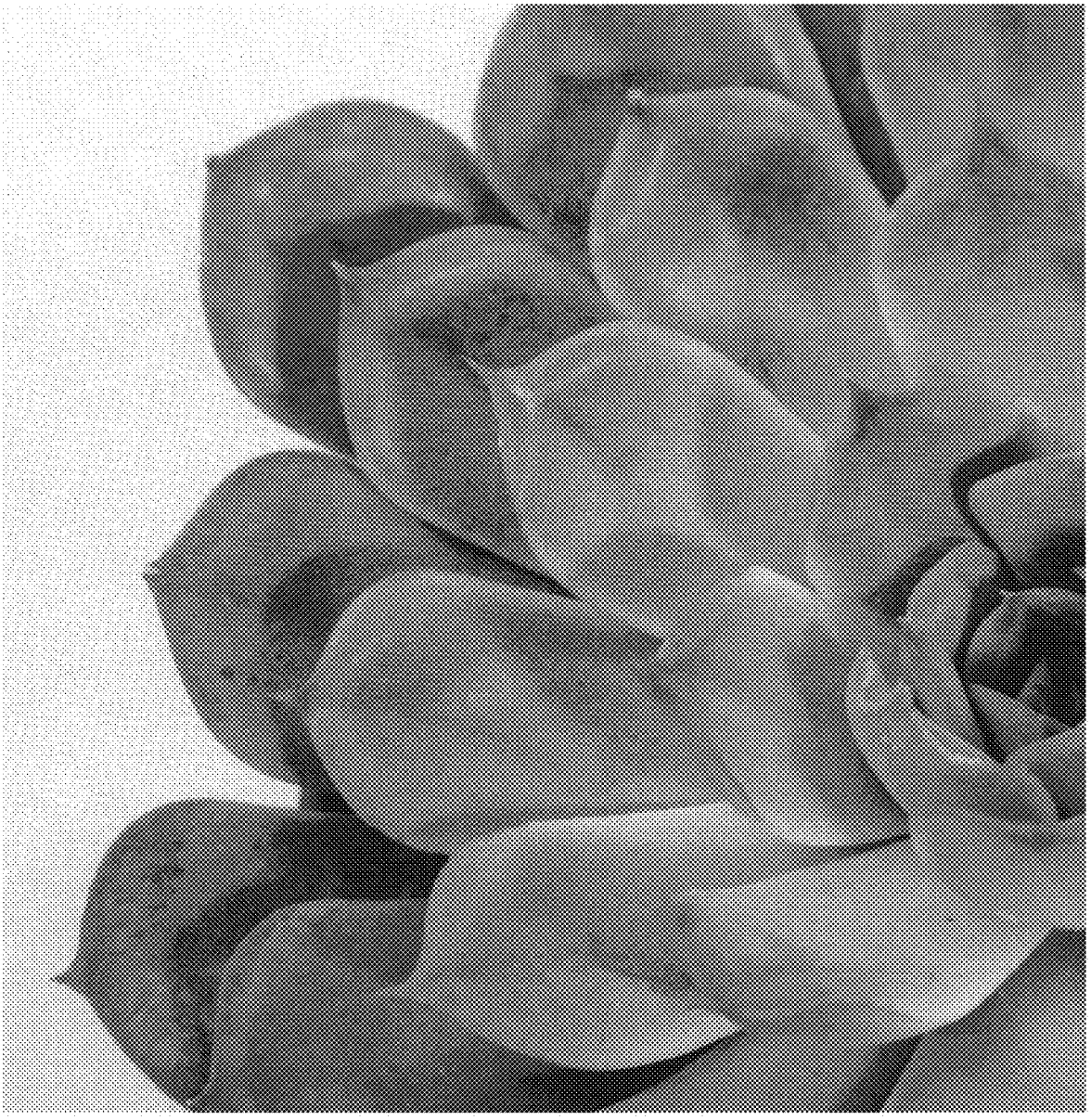
FIG. 3 illustrates, as nearly true as it is reasonably possible to make the same in color photographs of this type, the adaxial surface of the juvenile and mature foliage of 'TSAECH1820'.
Figure 4:
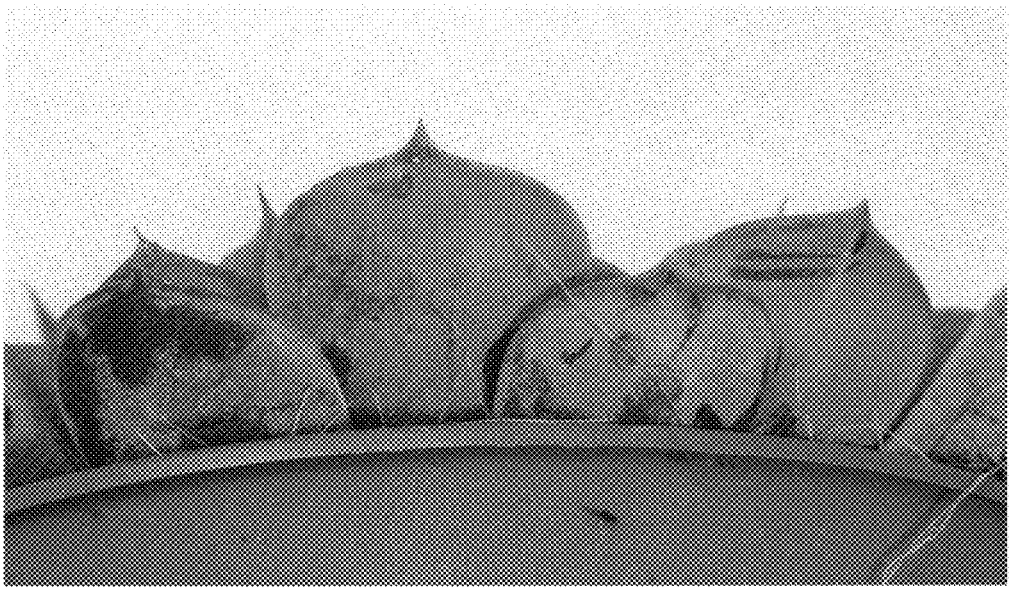
FIG. 4 illustrates, as nearly true as it is reasonably possible to make the same in color photographs of this type, the abaxial surface of the mature foliage of 'TSAECH1820'.

The following observations and measurements made in December of 2018 describe averages from a sample set of six specimens of 12 months old 'TSAECH1820' plants grown in 12 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1820' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'TSAECH1820' and comparisons with the parent plants and closest known comparator are provided below.

Plant description:

*Growth habit*.—Succulent perennial with foliage growing in a stemless basal rosette.

*Plant shape*.—Flattened.

*Height from soil level to top of foliar plane*.—4.7 cm.

*Plant spread*.—Average of 14.0 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 10.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Foliage:

*Arrangement*.—Rosette.

*Division*.—Simple.

*Attachment*.—Sessile.

*Quantity*.—Approximately 50 leaves per rosette.

*Shape*.—Obovate to broad oblanceolate.

*Dimensions*.—5.8 cm long, 2.4 cm wide, and 0.7 cm thick, on average.

*Aspect*.—Slightly concave and very slightly curved upwards.

*Attitude*.—Juvenile foliage at the center of the rosette is held upward and outward; foliage becomes progressively more relaxed towards the outer whorls of mature foliage, at an average angle of 20 degrees to horizontal.

*Apex*.—Apiculate.

*Base*.—Long cuneate.

*Margin*.—Entire; not undulated.

*Pubescence, texture and luster of the adaxial surface*.—Glabrous, smooth, and matte; moderately to heavily glaucous.

*Pubescence, texture and luster of the abaxial surface*.—Glabrous, smooth, and matte; moderately to heavily glaucous.

*Color*.—Juvenile foliage, adaxial surface — Nearest to in between greyed-green and yellow-green, RHS 191A and 148B, and fading to a lighter shade of yellow-green towards the base, nearest to RHS N148D; distally margined and tipped greyed-red, nearest to RHS 182B; the epicuticular wax covering the leaf surface is nearest to in between blue-green and greyed-green, RHS 122D and 188C. Juvenile foliage, abaxial surface — Yellow-green, nearest to RHS 148B, and fading to a lighter shade of yellow-green towards the base, nearest to RHS N148D; distally margined greyed-red, nearest to RHS 181C, and tipped a darker shade of greyed-red, nearest to RHS 182A; the epicuticular wax covering the leaf surface is nearest to in between blue-green and greyed-green, RHS 122C and 188D. Mature foliage, adaxial surface — Yellow-green, nearest to RHS 148A, and fading to a lighter shade of yellow-green towards the base, nearest to RHS 146C; margined greyed-red, nearest to a mixture of RHS 181B and 181C; the epicuticular wax covering the leaf surface is nearest to in between blue-green and greyed-green, RHS 122D and 188C. Mature foliage, abaxial surface — Yellow-green, nearest to RHS 147C, and heavily suffused with greyed-red towards the apex, nearest to a mixture of RHS 178A and 178B; margined greyed-red, nearest to a mixture of RHS 181B and 181C; the epicuticular wax covering the leaf surface is nearest to in between blue-green and greyed-green, RHS 122C and 188D.

*Venation*.—No venation is visible.

*Petiole*.—No petiole; leaves are sessile.

Inflorescence: No flowering has been observed to date.

Comparisons with the parent plant and closest known comparator:

Plants of the new cultivar 'TSAECH1820' differ from the seed parent, an unnamed *Echeveria pulidonis* plant (not patented), in the following characteristics described in Table 1 below.

TABLE 1

| Characteristic | 'TSAECH1820' | Seed parent |
|---|---|---|
| General coloration of the foliage. | A mixture of blue-gray and greyed-green, although darker than the parent. | Blue-green. |
| General coloration of the margins. | Pink. | Red. |

Plants of the new cultivar 'TSAECH1820' differ from the pollen parent, an unnamed *Echeveria laui* plant (not patented), in the following characteristics described in Table 2 below.

TABLE 2

| Characteristic | 'TSAECH1820' | Pollen parent |
|---|---|---|
| Plant vigor. | More vigorous than the pollen parent; lower mortality rate under adverse climatic conditions. | Less vigorous than 'TSAECH1820'; higher mortality rate under adverse climatic conditions. |
| Abundance of foliage. | More abundant than the pollen parent. | Less abundant than 'TSAECH1820'. |

TABLE 2-continued

| Characteristic | 'TSAECH1820' | Pollen parent |
|---|---|---|
| Foliage dimensions. | Longer and more narrow than the pollen parent. | Shorter and broader than 'TSAECH1820'. |
| General coloration of the foliage. | Generally appearing as a mixture of blue-gray and greyed-green, although darker than the parent. | Generally appearing as verily pale blue-gray to nearly white. |

Comparisons with the closest known comparator:

Plants of the new cultivar 'TSAECH1820' differ from the closest known commercial comparator, *Echeveria* sp. 'Orion' (U.S. Pat. No. PP26,228), in the following characteristics described in Table 3 below.

TABLE 3

| Characteristic | 'TSAECH1820' | 'Orion' |
|---|---|---|
| General coloration of the foliage. | Generally appearing as a mixture of blue-gray and greyed-green, although darker than 'Orion'. | Generally appearing as a mixture of blue-gray and greyed-green, although lighter than 'TSAECH1820'. |
| General coloration of the margins. | Generally appearing as a darker shade of pink. | Generally appearing as a lighter shade of pink. |

That which is claimed is:

1. A new and distinct variety of *Echeveria* plant named 'TSAECH1820', substantially as described and illustrated herein.

* * * * *